(12) United States Patent
Kibler et al.

(10) Patent No.: US 12,144,980 B2
(45) Date of Patent: *Nov. 19, 2024

(54) MULTI-ELECTRODE STIMULATION THERAPY WITH REDUCED ENERGY

(71) Applicant: BIOTRONIK SE & CO. KG, Berlin (DE)

(72) Inventors: Andrew B. Kibler, Lake Oswego, OR (US); Marcelo Baru, Tualatin, OR (US); Dirk Muessig, West Linn, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/309,229

(22) Filed: Apr. 28, 2023

(65) Prior Publication Data

US 2023/0264015 A1    Aug. 24, 2023

Related U.S. Application Data

(63) Continuation of application No. 16/952,140, filed on Nov. 19, 2020, now Pat. No. 11,745,007, which is a
(Continued)

(51) Int. Cl.
*A61N 1/05*  (2006.01)
*A61N 1/02*  (2006.01)
*A61N 1/36*  (2006.01)

(52) U.S. Cl.
CPC .......... *A61N 1/0529* (2013.01); *A61N 1/025* (2013.01); *A61N 1/3605* (2013.01);
(Continued)

(58) Field of Classification Search
CPC .. A61N 1/025; A61N 1/3605; A61N 1/36139; A61N 1/36153; A61N 1/36178
See application file for complete search history.

(56) References Cited

U.S. PATENT DOCUMENTS 6,516,227 B1    2/2003   Meadows et al.
2008/0015641 A1* 1/2008  Armstrong ......... A61N 1/36153
                                                  607/2
(Continued)

FOREIGN PATENT DOCUMENTS

WO    2016168485 A1    10/2016

*Primary Examiner* — Tammie K Marlen
(74) *Attorney, Agent, or Firm* — Laurence A. Greenberg; Werner H. Stemer; Ralph E. Locher

(57) ABSTRACT

A device for neurostimulation has a number N of electrodes. N is equal to or larger than 3. The device is configured to deliver via each electrode therapeutic electric phases of amplitudes $I_1, I_2, \ldots I_N$, with a frequency f and after each therapeutic electric phase a number of N−1 charge balancing electric phases. The charge balancing electric phases of the respective electrode each have a polarity that is opposite the polarity of the preceding therapeutic electric phase of the respective electrode. The device is configured to return for each electrode the current of each therapeutic electric phase in the other N−1 electrodes.

20 Claims, 12 Drawing Sheets

Related U.S. Application Data continuation of application No. 15/916,548, filed on Mar. 9, 2018, now Pat. No. 10,870,000.

(60) Provisional application No. 62/476,885, filed on Mar. 27, 2017.

(52) U.S. Cl.
CPC ........ *A61N 1/36062* (2017.08); *A61N 1/0551* (2013.01); *A61N 1/36142* (2013.01); *A61N 1/36164* (2013.01); *A61N 1/36171* (2013.01)

(56) References Cited

U.S. PATENT DOCUMENTS

| | | |
|---|---|---|
| 2011/0106214 A1 | 5/2011 | Carbunaru et al. |
| 2012/0046711 A1* | 2/2012 | Osorio ................ A61B 5/4836 607/45 |
| 2016/0015980 A1 | 1/2016 | Biele et al. |
| 2018/0117332 A1 | 5/2018 | Robinson et al. |

* cited by examiner

MULTI-ELECTRODE STIMULATION THERAPY WITH REDUCED ENERGY

CROSS-REFERENCE TO RELATED APPLICATION

This application is a continuation of copending U.S. patent application Ser. No. 16/952,140, filed on Nov. 19, 2020, now U.S. Pat. No. 11,745,007, which application is a continuation of U.S. patent application Ser. No. 15/916,548, filed Mar. 9, 2018, now U.S. Pat. No. 10,870,000, registered on Dec. 22, 2020, the present application also claims the priority, under 35 U.S.C. § 119(e), of provisional patent application No. 62/476,885 filed Mar. 27, 2017; the prior applications are herewith incorporated by reference in their entireties.

BACKGROUND OF THE INVENTION

Field of the Invention

The system and method according to the invention is directed to neurostimulation, as for example, spinal cord stimulation (SCS), peripheral nerve stimulation (PNS) with vagus nerve stimulation (VNS) in particular, or deep brain stimulation (DBS).

Spinal cord stimulation (SCS) as a means of pain relief for patients suffering from neuropathic pain has traditionally been practiced as a therapy requiring paresthesia sensations to overlap a patient's region of pain in order to provide relief. Recent research has shown that an alternate mechanism of pain relief is available through which high-frequency paresthesia-free stimulation is effective in patients without requiring intra-operative electrode mapped selection.

Spinal cord stimulation (SCS) has traditionally utilized stimulation pulses delivered at 40 to 60 Hz to induce paresthesias overlapping a patient's regions of pain. Traditional paresthesia-based SCS therapy makes use of dorsal column axon recruitment to induce a tingling sensation overlapping with the region of nociception and thus reducing the perception and experience of pain. Its effect begins in minutes and the paresthesia sensation is typically tolerated by the patient for the continued reduction of their perception of pain. Patients may adjust the stimulation amplitude using a patient remote control to a greater level to enhance their pain relief during periods of heighted pain, and may reduce the amplitude and sensation of paresthesia during periods of restfulness or decreased pain, or may adjust the stimulation amplitude based on different body positions which influence lead position relative to the spinal cord. Due to the fact that paresthesia is an unnatural sensation, patients prefer to use this control to minimize it.

The mechanism of action of paresthesia-based stimulation is as follows: electrical fields generated by SCS leads over the dorsal columns of the spinal cord excite action potentials in axially-oriented dorsal column axons, which are associated with conduction of sensory information to the brain. These action potentials propagate to the brain, inducing paresthesia sensations, as well as retrograde into the dorsal horn network of the spinal columnar grey matter. This retrograde propagation reaches excitatory synapses connected from the dorsal column axons to inhibitory interneurons, the excitation of the inhibitory interneurons facilitates inhibition of pain relay neurons.

In the last few years, additional therapies have demonstrated efficacy of a paresthesia-free method of pain relief whereby the patient does not experience paresthesias and the stimulation electrodes selected may not map directly to a dermatomal alignment with the patient's region of pain. High-frequency SCS therapy utilizes stimulation frequencies between 1.5 kHz and 100 kHz, preferred 10 kHz, to achieve a neuromodulatory effect without recruiting the dorsal column fibers associated with paresthesia. Research indicates that this therapy modality reduces the wind-up hypersensitivity of dorsal horn interneurons responsible for relaying a painful sensation from the peripheral to the central nervous system. Pain relief associated with this stimulation may require several hours to a day to take effect.

The mechanism of action of this mode of therapy is still under debate; however the prevailing theory is as follows. High-frequency SCS stimulation has little influence on the dorsal column axons which facilitate paresthesia therapy, instead directly inducing slight potentiation changes on lamina I neurons in the dorsal horn of the spinal cord. The potentiation changes trigger a cascade of intracellular signalling responses which induce a direct inhibition of sensitization and suppression of activity of neuropathic pain relay neurons in the dorsal horn.

This paresthesia-free SCS approach is similar in frequencies to high-frequency transcutaneous spinal electroanalgesia (TSE) which has been available for decades. Whether the underlying mechanisms and site of pain relief action are the same between high-frequency TSE and high-frequency SCS remains to be determined.

Drawbacks of 10 kHz stimulation are as follows: it requires very high frequency stimulation control, energy is wasted through parasitic capacitive charge and discharge as a result of frequent polarity transitions of current delivery, and most important neuronal response is not efficient at 10 kHz stimulation frequency given the anodic pulse amplitude (utilized for charge balancing) is constrained by timing to be the same as the cathodic pulse amplitude, which influences cathodic stimulation thresholds.

The consequences of a high-energy SCS implantable device include frequent recharging and large device size, both of which can have a significantly negative patient impact. The number of recharge cycles is also limited requiring the patient to have more frequent revision surgeries for device replacement.

Furthermore, electrical stimulation requires charge balancing to terminate electrochemical reactions that may cause hazardous conditions for both tissue and electrodes. High-frequency stimulation is constrained in timing requiring active balance phases instead of the passive balance phases utilized in traditional 40 to 60 Hz SCS. Active balance phases are driven with a current source, whereas passive balance phases are driven by accumulated charge across a capacitor, commonly a DC blocking capacitor in series with each stimulating electrode. At 10 kHz, the timing between the stimulating and balance phase (i.e. the inter-phase interval) is very short causing the balance phase amplitude to influence the effect desired to be caused by the stimulating phase. This implies higher energy is required which translates into frequent device recharges and large implantable device size to fit larger batteries to support continuous stimulation. These drawbacks are associated with higher patient burden of recharging, an increased chance of uncomfortable implantable device pocket placement or device erosion through the skin due to its large size, and a reduced service time requiring the patient to have revision surgeries more often for device replacement.

Known commercial solutions relate to 'HF-10' paresthesia-free therapy, with stimulation duty cycling, as well as burst therapy 'Burst DR' (paresthesia-free in most patients).

One technique applied to reduce battery capacity requirements is the practice of turning off therapy for a short period of time during which the carry-over effect of stimulation will continue to provide pain relief. The result is, for example, HF-10 therapy with duty cycling permits lower charge usage with a given stimulation amplitude as a factor of the time spent with the stimulation off vs the time spent while stimulation is on. The problem with this approach is that it is likely this also reduces overall pain relief to the patient as a result of the overall reduced therapeutic dose.

Burst DR therapy, while using sub-kHz frequencies and lower energy than HF-10 therapy, may suffer from poorer pain relief performance as evidenced by reported responder rates and levels of reduced pain relief in lower back and leg pain patients.

SUMMARY OF THE INVENTION

Based on the above, it is an objective of the present invention to provide a stimulation approach which reduces patient recharging burden and allows for reduced implantable device size by improving on the efficiency of the core treatment.

This problem is solved by a device having the features of the main claim as well as by a method having the features of the main method claim. Embodiments of these aspects of the present invention are stated in the corresponding sub claims and/or are described below.

Accordingly, a device for neurostimulation is disclosed comprising at least a number N of electrodes, wherein N is a natural number that is equal or larger than 3. The device is configured to deliver via each of N electrodes a therapeutic electric phase of electrode-corresponding amplitude $I_1$, $I_2$, ..., $I_N$, having a frequency (phases per second) f and after each therapeutic electric phase a number of N−1 electric charge balancing phases. The charge balancing electric phases of the respective electrode each have a polarity that is opposite the polarity of the preceding therapeutic electric phase of that electrode, and wherein the device is configured to return for each electrode the electrical current of each therapeutic electric phase via the other N−1 electrodes.

Particularly, the therapeutic electric phases can be cathodic phases. Then, the charge balancing electric phases are anodic electric phases. Of course it is also possible that the therapeutic electric phases are anodic phases. Then, the charge balancing electric phases are cathodic electric phases.

According to an aspect, the proposed invention is applied for neurostimulation, as for example, spinal cord stimulation (SCS), peripheral nerve stimulation (PNS) with vagus nerve stimulation (VNS) in particular, or deep brain stimulation (DBS).

Particularly, according to an aspect of the invention, a paresthesia-free SCS approach is disclosed which is able to achieve efficient paresthesia-free pain relief having frequencies below or equal 1,500 Hz (preferably 1,000 Hz to 1,450 Hz, further preferred 1,450 Hz) by utilizing a novel stimulation charge-balancing approach. Particularly, this approach utilizes multiple electrodes to provide cathodically-weighted, charge-balanced therapeutic stimulation whereby the stimulation return current and charge balancing occurs particularly at the same time and in a distributed fashion.

Particularly, the primary benefit of the present invention is improved pain therapy by delivering paresthesia-free pain relief in an efficient manner, distributed across a broader region of the spinal cord for maximum effect. In addition, the reduced current amplitude of the charge balancing phase compared to the therapeutic phase allows for more efficient actuation of neuron membrane dynamics by not reversing the transmembrane potential influence with an opposite and equal current, as it is required with high-frequency stimulation. Efficient stimulation reduces device recharging burden on the patient, as well as reducing implant size requirements, improving their therapeutic experience.

Furthermore, particularly, the present invention describes a novel SCS therapeutic stimulation approach which delivers pain relieving neuromodulation at high frequencies and with lower energy requirements compared to the current state-of-the-art. This is because in the novel waveform disclosed, the distributed balance phase does not influence the stimulating phase threshold and the return currents circulated during the different phases allow charge balancing the participating electrodes making the novel waveform, unlike prior art, self-balancing stimulation.

Known to those skilled in the art are implantable spinal cord stimulators, with associated percutaneous or paddle leads implanted in the supra-dural space in patients' vertebral lumen. These known components and their associated supporting chargers and patient remote controls will not be described herein. Particularly, the present invention makes use of these components to provide spinal cord stimulation (SCS) to patients using a plurality of therapeutic stimulation phases in a distributed manner across a plurality of electrodes, such that the charge balancing phase of any given electrode is distributed, and each portion of the charge balancing phase is also the current return of a stimulating electrode, at the same time. Particularly, this approach departs from traditional neuromodulation stimulation whereby each stimulation phase and its charge balancing phase occur on a sequential basis symmetrically across electrodes.

Particularly, according to an embodiment, the stimulation approach according to the present invention can comprise the following features:

a) A number of electrodes N are utilized for stimulation; preferably N is larger than 2;

b) Each electrode undergoes a therapeutic phase (therapeutic electric pulses) of amplitude $I_1$, $I_2$, ... $I_N$ at a frequency f and charge balancing phases (charge balancing electric pulses) of an opposite polarity;

c) The current of each therapeutic phase is returned by the charge balancing phases in the other N−1 electrodes, distributed preferably with equal weight I/(N−1); and d) The integrated average charge delivered by the therapeutic and charge balancing phases is zero over time.

Furthermore, according to an embodiment, the preferred timing between any two (2) successive therapeutic phases from different electrodes is 1/Nf.

Further, according to an embodiment, the therapeutic and charge balancing phases are separated by inter-phase intervals; particularly with a minimum duration in the tens of µs for the highest preferred frequency f of 1,450 Hz.

Furthermore, according to an embodiment, charge delivered via the N electrodes may be further passive-balanced during at least one (1) of the inter-phase intervals.

Particularly, due to the device's configuration, the charge balancing electric phases for charge balancing have in sum the same amount of charge than the respective therapeutic stimulation electric phase.

Furthermore, according to an embodiment of the present invention, the device is configured to deliver for each therapeutic electric phase of each of the N electrodes a charge balancing electric phase in all other N−1 electrodes at the time of the respective therapeutic electric phase. Particularly, as already described above, the device is configured to deliver the charge balancing electric phases with an amplitude of I/(N−1) (i.e. amplitude I of the respective therapeutic electric phase divided by the number N−1 of charge balancing electric phases).

Furthermore, according to an embodiment of the present invention, the device is an implantable device.

Further, according to an embodiment of the present invention, the device is configured to generate therapeutic electric phases with an amplitude I that lies preferably within the range from 0.1 mA to 20.0 mA.

Furthermore, according to an embodiment, the device provides at least one (1) parameter configuration for neurostimulation, particularly spinal cord stimulation (SCS), which parameter configuration is stored in the device. Particularly, this parameter configuration allows to conduct neurostimulation, particularly SCS, according to the method of the present invention (see also below).

A further aspect of the present invention relates to a method for delivering neurostimulation (wherein the method particularly uses a device according to the present invention) using a number N of electrodes, wherein N is a natural number equal or larger than 3. Wherein via each electrode therapeutic electric phases (therapeutic electric pulses) of amplitude $I_1, I_2, \ldots, I_N$ are delivered with a frequency f followed by a number of N−1 charge balancing electric phases (also denoted as charge balancing phases) after each therapeutic electric phase. The charge balancing electric phases of the respective electrode each have a polarity that is opposite the polarity of the preceding therapeutic electric phase of that electrode, and wherein for each electrode the electrical current of each therapeutic electric phase is returned via the other N−1 electrodes.

Particularly, as already indicated above, the therapeutic electric phases can be cathodic phases. Then, the charge balancing electric phases are anodic electric phases. Of course, it is also possible that the therapeutic electric phases are anodic phases. Then, the charge balancing electric phases are cathodic electric phases.

Particularly, the charge balancing electric phases for charge balancing have in sum the same amount of charge than the respective therapeutic stimulation electric phase.

According to an embodiment of the method according to the present invention the device is configured to deliver for each therapeutic electric phase of each of the N electrodes a charge balancing electric phase in all other N−1 electrodes at the time of the respective therapeutic electric phase.

According to an embodiment of the method according to the present invention the device is configured to deliver the charge balancing electric phases with an amplitude of I/(N−1) (i.e. amplitude I of the respective therapeutic electric phase divided by the number N−1 of charge balancing electric phases).

According to an embodiment of the method according to the present invention the device is configured to deliver the therapeutic and charge balancing electric phases such that the integrated average current delivered by the therapeutic and charge balancing electric phases is zero over time.

Particularly, according to an embodiment of the method according to the present invention, the therapeutic electric phases are delivered such that the time interval between any two (2) successive therapeutic phases from different electrodes is 1/Nf (i.e. the inverse of, the number N of electrodes multiplied by the frequency f).

Further, according to an embodiment of the method according to the present invention, the therapeutic and charge balancing phases are delivered such that the therapeutic electric phases and the charge balancing electric phases are separated by inter-phase intervals.

Further, according to an embodiment of the method according to the present invention, charge delivered via the N electrodes is passive-balanced during at least one (1) of the inter-phase intervals.

Further, according to an embodiment of the method according to the present invention, the delivered neurostimulation is spinal cord stimulation (SCS).

Further, according to an embodiment of the method according to the present invention, the method is conducted using an implanted device for neurostimulation, particularly spinal cord stimulation (SCS).

Further, according to an embodiment of the method according to the present invention, the frequency f is below or equal to 1,500 Hz, according to an embodiment of the present invention the frequency lies within the range from 1,000 Hz to 1,450 Hz. Particularly, according to a preferred embodiment, the amplitude I of the therapeutic electric phases lies within the range from 1.0 mA to 20.0 mA. Preferably, according to a further embodiment of the invention, the amplitude I of the therapeutic electric phases lies within the range from 1.0 mA to 5.0 mA.

A significant benefit of this invention, beyond power saving due to lower frequencies already described, is that the medium-distance electric field influence of the stimulation provided exhibits a cathodic or anodic preference, or bias. Electrodes delivering the therapeutic phase of stimulation, whether it is anodic or cathodic in nature, are delivering a higher current than the return currents (charge balancing phases) received by the greater number of other individual electrodes participating in the stimulation. This higher therapeutic current will induce a bias in the medium-distance field of stimulation, driving cellular response to be primarily hyperpolarizing or primarily depolarizing in nature. This influence is the principal reason why common traditional stimulation practiced in the field utilizes a larger surface area anode than cathode. Our approach accomplishes a similar bias but distributed among several electrodes which are participating in the novel stimulation waveform cycle.

According to an embodiment of the present invention, the stimulation waveform may employ pulse width modulation of the therapeutic and/or charge balancing phases for stimulation focus control.

Other features which are considered as characteristic for the invention are set forth in the appended claims.

Although the invention is illustrated and described herein as embodied in a multi-electrode stimulation therapy with reduced energy, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
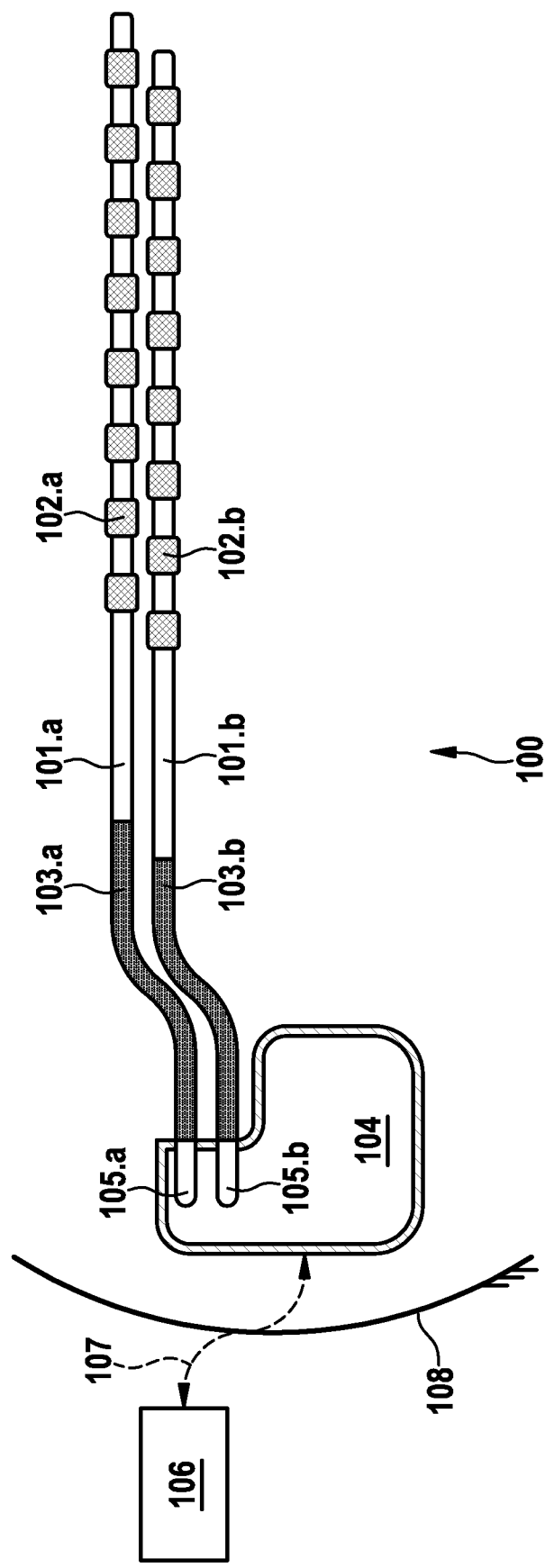
FIG. 1 is an illustration showing a SCS implantable system/device.

Referring now to the figures of the drawings in detail and first, particularly to FIG. 1 thereof, there is shown an example of an implantable system/device 100 for spinal cord stimulation (SCS). Such a system/device includes first and second implantable percutaneous leads 101.a and 101.b that are implanted into a targeted location in the epidural space. Such leads 101 may be replaced by a paddle lead or other type of SCS leads.

The distal portion of the leads 101.a and 101.b incorporate a plurality of electrodes 102.a and 102.b respectively. Octal leads 101 (eight electrodes each) are shown in the example illustrated in FIG. 1. Each electrode 102 is connected to an insulated wire (not shown), which wires run inside flexible insulated carriers 103.a and 103.b. These carriers 103 get tunnelled during implantation to the vicinity of the implantable pulse generator (IPG) 104 that is typically implanted subcutaneously in the patient's lower abdominal or gluteal region. Carriers 103.a and 103.b terminate proximally in connectors 105.a and 105.b respectively that are then inserted into the IPG 104 header to allow conducting electrical charge to electrodes 102.

The IPG 104 can communicate with external devices 106 through suitable radio frequency (RF, e.g. MICS-band) or inductive links 107 that pass through the patient's skin 108. The external devices 106 may include a clinician programmer, a patient remote control, or an external charger among others. An external charger will send power transcutaneously though an inductive link 107 for battery recharge given the IPG 104 is preferably powered by a secondary battery.

Figure 2:
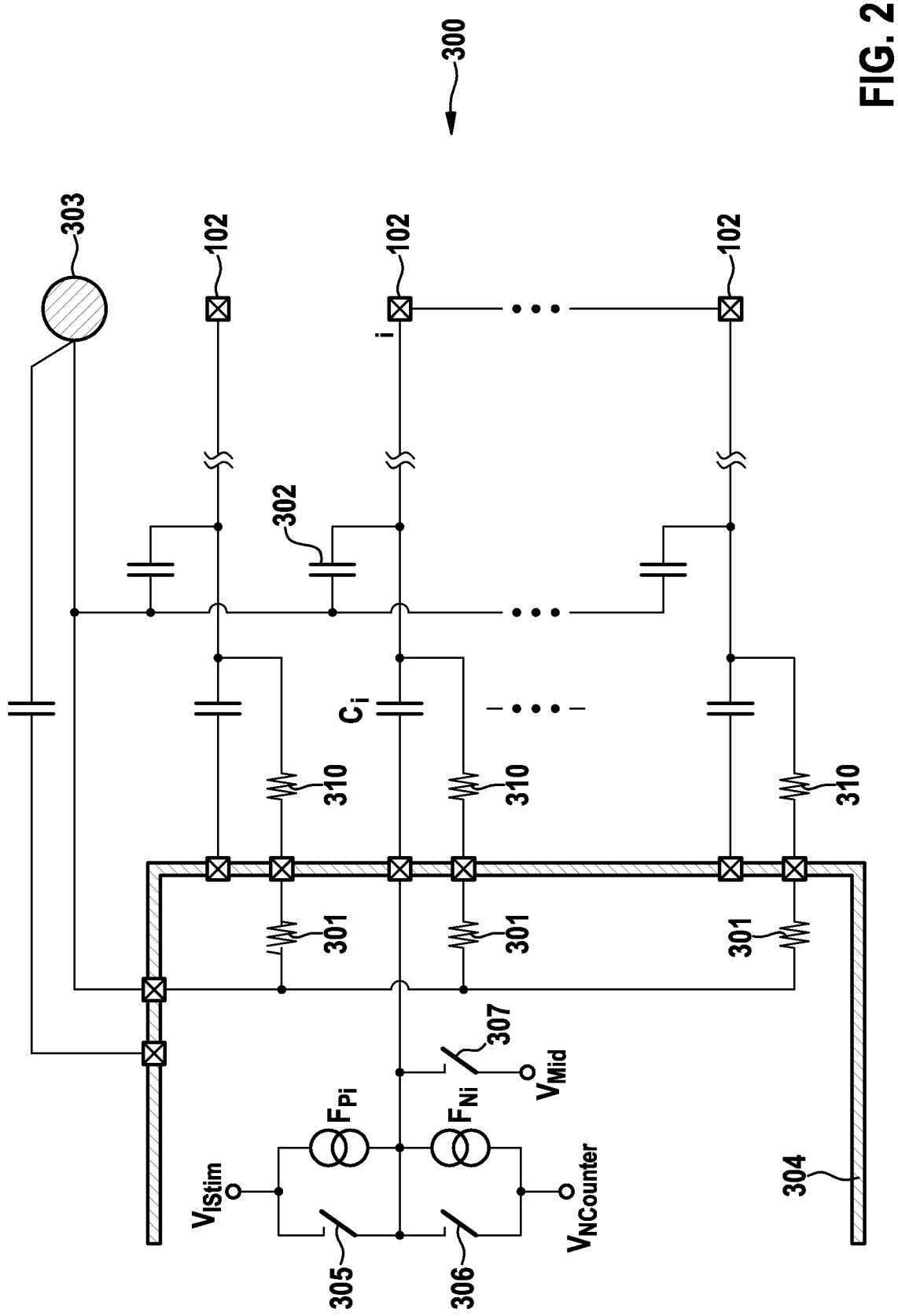
FIG. 2 is a circuit diagram of an implantable pulse generator (IPG) front-end for SCS.

The electrodes 102 are electrically driven by a front-end 300 (in the IPG 104), which is shown in FIG. 2. Component $C_i$ represents the DC blocking capacitor in series with each of the electrodes i (102) traditionally employed to deliver electrical stimulation.

Resistors 301 in FIG. 2 are bleeding resistors (hundreds of kΩ), placed in star configuration, typically utilized in IPG's front-end 300 for passive charge neutrality. Capacitors 302, also in star configuration, provide filtering against electromagnetic interference (transitory voltage suppression protections, such as against external defibrillation pulses and electrostatic discharges, are not shown for simplicity). The common mode of both resistors 301 and capacitors 302 star configurations are connected to the conductive area 303 of the IPG 104 case.

An application specific integrated circuit (ASIC) 304 provides five controllable elements for biphasic stimulation where only one (1) may be active at any time when the respective electrode 102 is utilized for therapy delivery. Current $F_{Pi}$ permits sourcing current through an electrode i (102) from the programmable voltage $V_{IStim}$ whereas current $F_{Ni}$ permits sinking current to a programmable voltage $V_{NCounter}$, which may be system ground Vss, as desired. Having sourcing and sinking currents independently controllable at each electrode i (102) permits delivering simultaneous multi-electrode SCS therapy with active charge balancing. Analog switches 305, 306 permit connecting an electrode i (102) to either $V_{IStim}$ or $V_{NCounter}$ respectively when currents of only one type are to be applied. Analog switches 307, referenced to a mid-voltage $V_{Mid}$, permit passive charge balancing. Voltage $V_{Mid}$ may be any voltage between $V_{IStim}$ and Vss including them. Resistors 310 may be added to limit the current in the presence of externally-generated fields (e.g. defibrillation).

Figure 3:
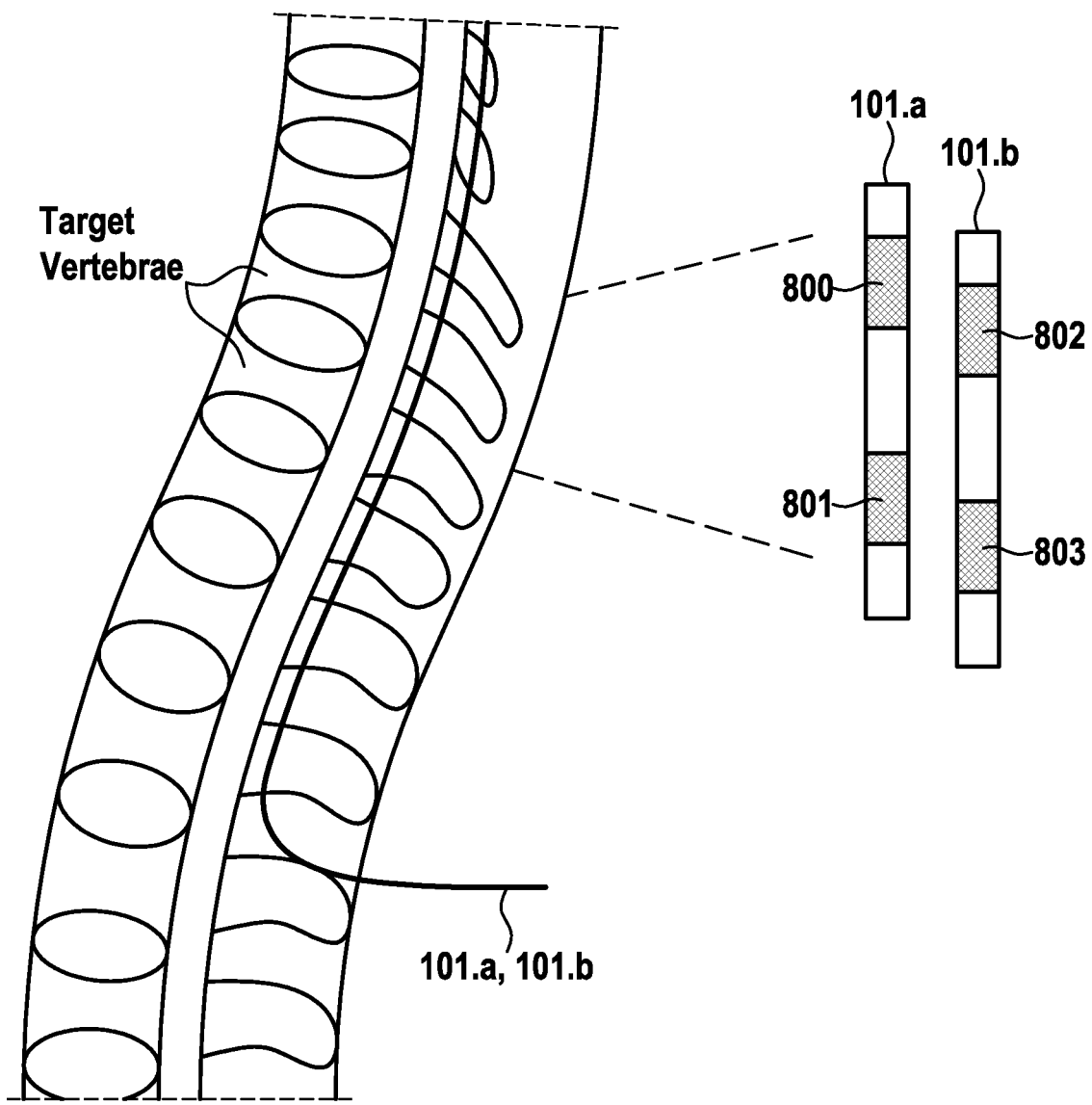
FIG. 3 is an illustration showing an example of positioned electrodes for therapy delivery, using the novel stimulation waveform, for chronic low and leg pain.

In the following, a preferred stimulation (for therapy) approach based on the novel stimulation waveform of the present invention, as presented in FIG. 8, e.g. for the treatment of chronic back and leg pain is described. Such therapy utilizes four (N=4) electrodes 102, namely 800, 801, 802, and 803 as shown in FIG. 3. Leads 101.a and 101.b are implanted and positioned so electrodes 102 in the thoracic region are utilized for therapy (i.e. electrodes 800-803).

According to an alternative embodiment of the stimulation approach, a single lead 101.a is utilized to deliver the novel stimulation waveform of the present invention.

Figure 4:
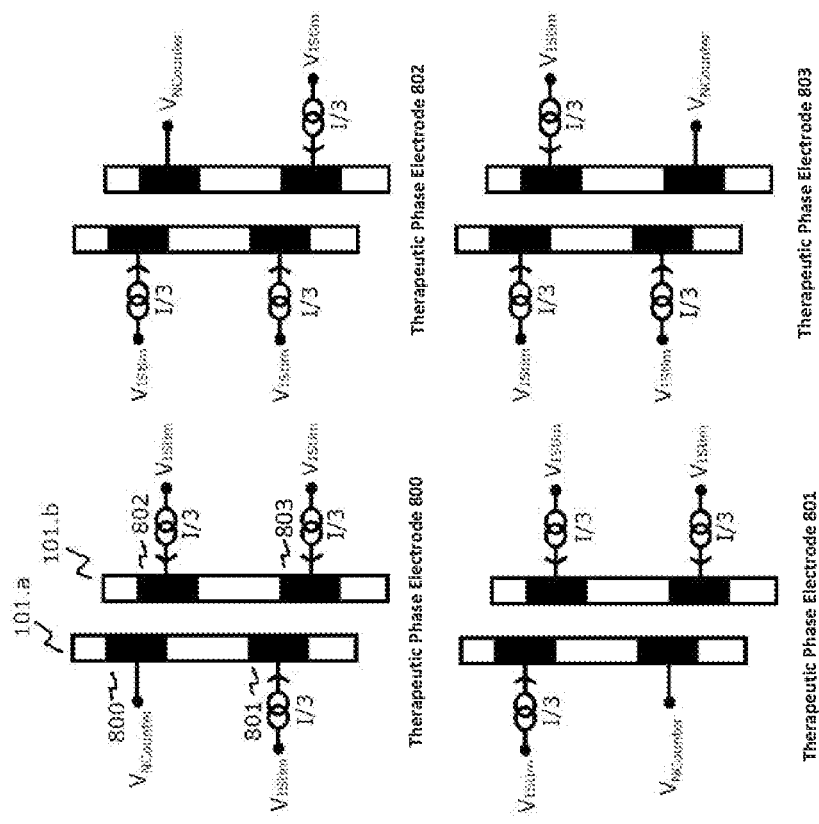
FIG. 4 is an illustration showing an example of electrode drive to implement novel waveform shown in FIG. 8 on four (4) electrode contacts.

The first therapeutic phase (therapeutic electric pulse) of the novel stimulation waveform, in the example, is that of electrode 800. To implement it, the elements $I_{Pi}$ (see FIG. 2) of electrodes 801-803 are programmed to the desired amplitude I divided by 3 (equal to I/(N−1)). Electrode 800 is connected to element $V_{NCounter}$ (see FIG. 2) in such phase so the total current I provides cathodic stimulation at electrode 800. The other therapeutic phases for electrodes 801-803 are shown in FIG. 4 and can be described in a similar way.

Figure 12:
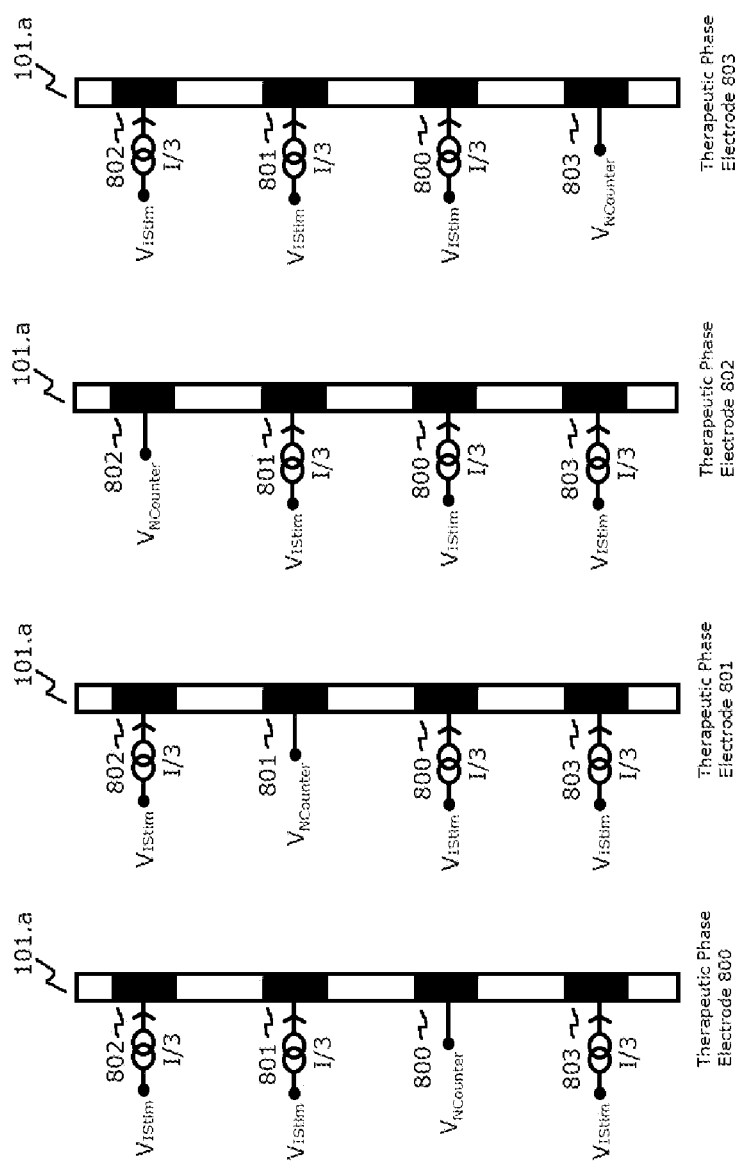
FIG. 12 is an illustration showing a lead arrangement according to an embodiment of the present invention where therapy is delivered using a single lead.

According to an embodiment of the present invention, the therapy is delivered using a single lead 101.a. FIG. 12 shows the preferred electrodes 102, namely electrodes 800, 801, 802, and 803 arrangement, and the different therapeutic phases (therapeutic electric pulse) starting from electrode 800, moving to electrode 803 and repeating. Adjacent electrodes 102 on the same lead 101.a are shown for simplicity but electrodes 800, 801, 802, and 803 are not required to be adjacent. Similar arrangements can be conceived using paddle leads.

The preferred passive balance, in at least one (1) of the inter-phase intervals, is performed by closing switches 307 (see FIG. 2) for the participating electrodes 800-803. This avoids voltage runaway in the DC blocking capacitors $C_i$ of the mentioned electrodes that may be caused by mismatches in the generation of the different I/3 (equal to I/(N−1)) among the different electrode i (102) drivers. It also keeps the electrode 800-803 potentials within acceptable ranges for continuous therapy delivery.

Figure 8:
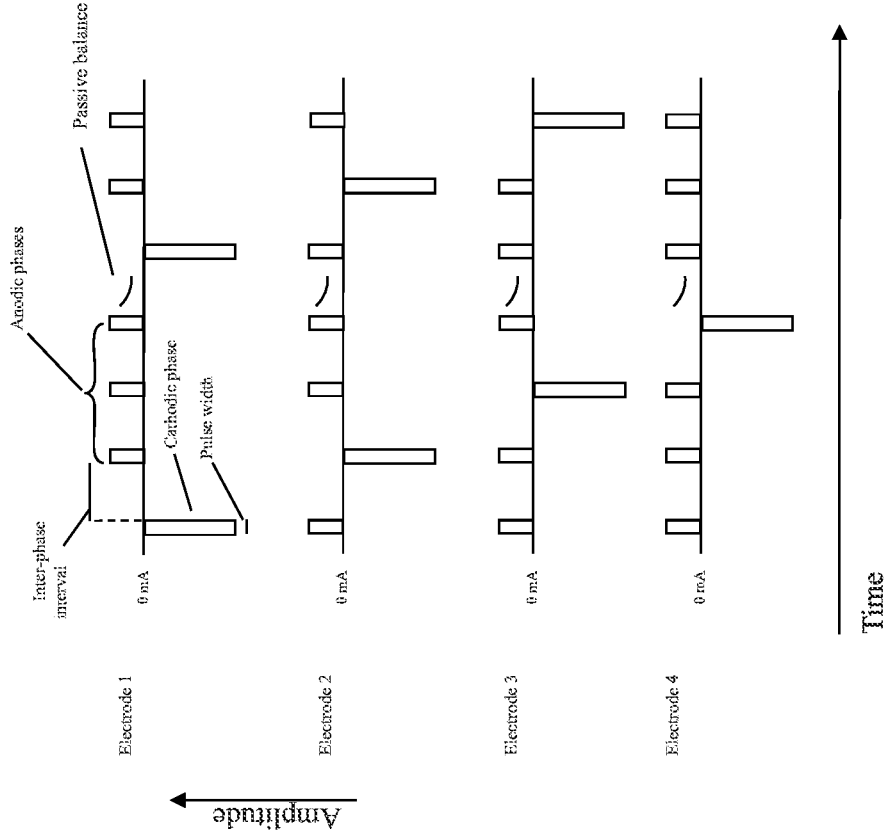
FIG. 8 is a diagram showing another embodiment of the novel stimulation waveform between four (4) electrodes, with cathodic preference.

The preferred timing parameters, for the example of FIG. 8 being described, are 30 μs and 140 μs, for the pulse width PW and inter-phase intervals, respectively. This results in an equivalent frequency f, for the therapeutic phase at each electrode 800-803, slightly above the preferred 1,450 Hz. The pulse width PW preferred range is from 15 μs to 1,000 μs whereas that of the inter-phase interval may start from tens of μs to hundreds of μs or even a few thousand μs.

The therapeutic phase amplitude I may be programmable in the order of less than 20.0 mA, preferably less than 10.0 mA, further preferred between 1.0 mA to 5.0 mA, or between 0.5 mA and 10.0 mA. The maximum charge injected in any therapeutic phase is also limited by the IPG 104 to avoid tissue and electrode damage.

The IPG 104 of the present invention is capable of delivering multi-modality SCS therapy. An exemplary regime for multi-modality SCS therapy is described in U.S. provisional application No. 62/476,884 which is herewith incorporated by reference in its entirety.

Figure 5:
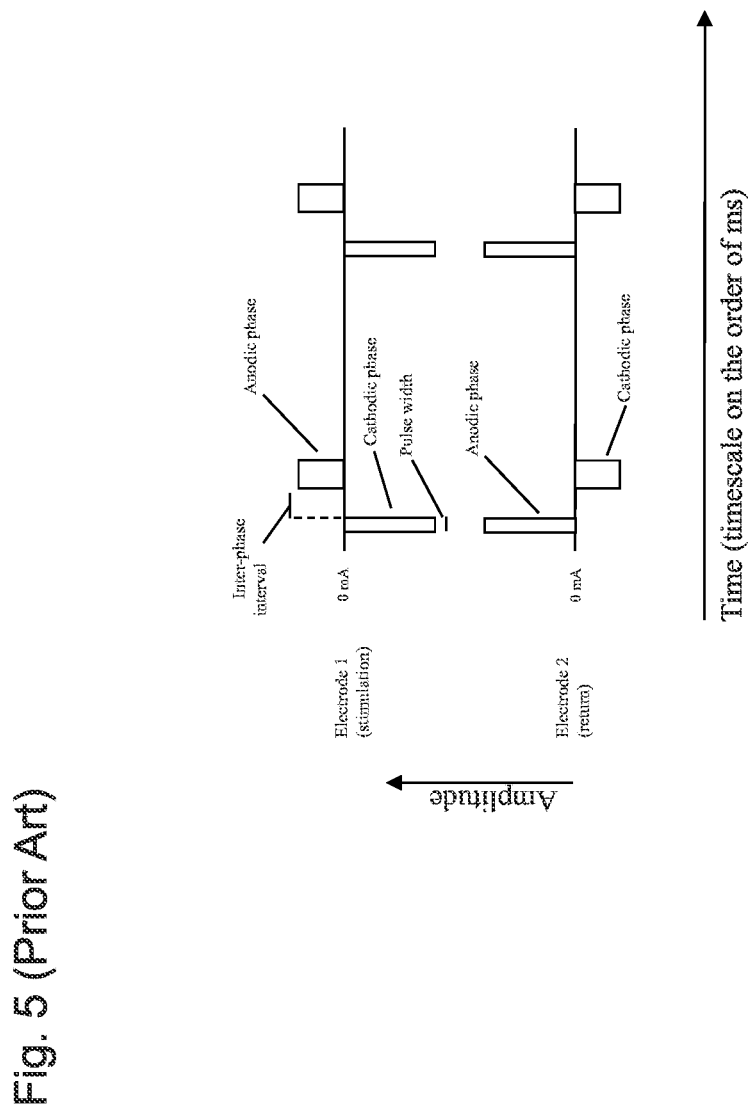
FIG. 5 is a diagram showing a low-frequency (paresthesia-based) stimulation waveform between two (2) electrodes as known from the prior art.

FIG. 5 shows a diagram of a low frequency stimulation waveform between two (2) electrodes known from the prior art. Stimulation begins with a cathodic phase, contains an inter-phase interval, and ends with an anodic (charge balancing) phase (charge balancing electric pulse), and repeats. The return electrode passes the same but opposite currents. Additional electrodes may share different amounts of current, but with the same timing and wave shape.

Figure 6:
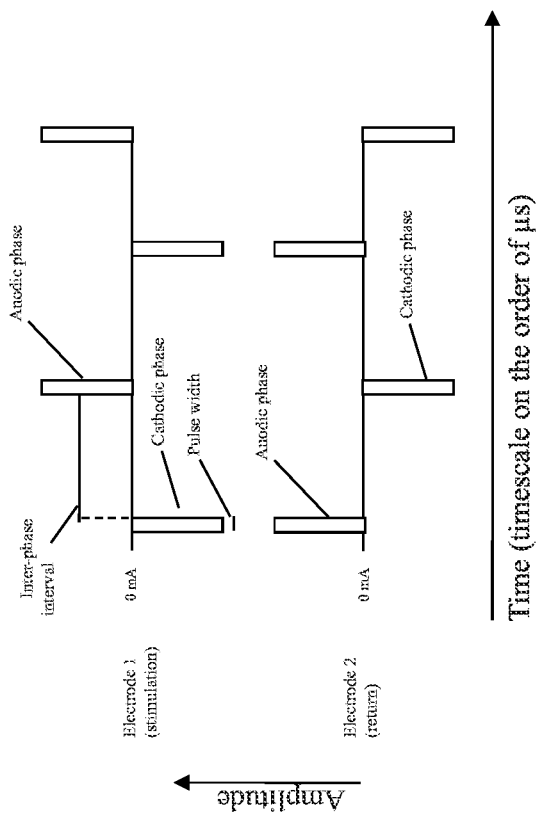
FIG. 6 is a diagram showing a high-frequency (paresthesia-free) stimulation waveform between two (2) electrodes as known from the prior art.

FIG. 6 shows a diagram of a high-frequency stimulation waveform between two (2) electrodes known from the prior art. Stimulation begins with a cathodic phase, contains an inter-phase interval, and ends with an anodic (charge balancing) phase (charge balancing electric pulse), and repeats. The return electrode passes the same but opposite currents. Additional electrodes may share different amounts of current, but with the same timing and wave shape.

In the approach according to an embodiment of the present invention a system/device comprises N electrodes, each of the N electrodes (preferably N larger than 2 electrodes) undergoes a recurring pattern of a therapeutic phase (therapeutic electric pulse) with a current amplitude I and a series of N−1 of charge balancing phases (charge balancing phases also denoted charge balancing electric pulses herein), which pass an inverted current amplitude I of the therapeutic phase, preferably distributed with equal weight (I/(N−1)). The therapeutic phase and the charge balancing phases are separated by one (1) inter-phase interval. Further, each therapeutic phase is timely aligned with one (1) charge balancing phase of the other N−1 electrodes such that in the system/device only on therapeutic phase occurs at a time. After every electrode cyclically passed one (1) therapeutic phase the cycle starts with the first of the N electrodes.

Figure 7:
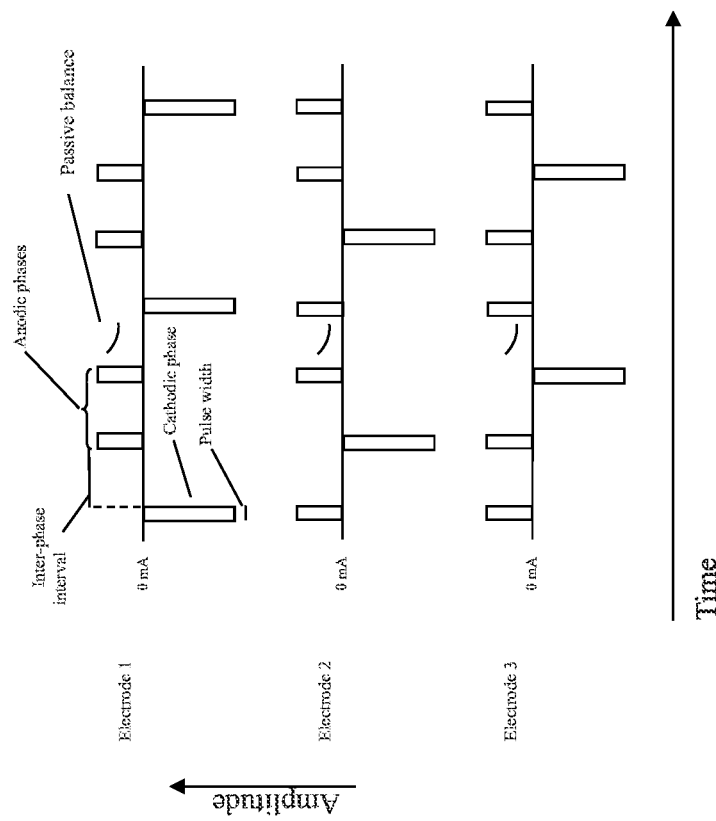
FIG. 7 is a diagram showing one embodiment of the novel stimulation waveform between three (3) electrodes, with cathodic preference.

FIG. 7 shows a diagram of one embodiment of the stimulation waveform according to the present invention between three (N=3) therapy electrodes, with cathodic preference. The exemplary system/device comprises three (3) electrodes (electrode 1, electrode 2, and electrode 3), each of the three (3) electrodes undergoes a recurring pattern of a cathodic phase (therapeutic phase, also denoted therapeutic electric pulse herein) with a current amplitude I and a series of two (2) charge balancing anodic phases (charge balancing phases, also denoted as charge balancing electric pulses herein), which pass ½ of the inverted current amplitude I of the therapeutic phase. The therapeutic phase and the charge balancing phases are separated by one (1) inter-phase interval. While electrode 1 passes the therapeutic phase with amplitude I, each of electrode 2 and electrode 3 passes one (1) charge balancing phase with amplitude I/2. While electrode 2 passes the therapeutic phase with amplitude I, each of electrode 1 and electrode 3 passes one (1) charge balancing phase with amplitude I/2. While electrode 3 passes the therapeutic phase with amplitude I, each of electrode 2 and electrode 1 passes one (1) charge balancing phase with amplitude I/2. After electrode 3 passed one (1) therapeutic phase the cycle starts with electrode 1 again, until terminated. In this way, charge neutrality on any given electrode is maintained, and the sum of current exiting the cathode equals the sum of currents entering anodes at any given time in the waveform.

FIG. 8 shows a diagram of another embodiment of the stimulation waveform according to the present invention between four (N=4) therapy electrodes, with cathodic preference. The exemplary system comprises four (4) electrodes (electrode 1, electrode 2, electrode 3, and electrode 4), each of the four (4) electrodes undergoes a recurring pattern of a cathodic phase (therapeutic phase, also denoted as therapeutic electric pulse herein) with a current amplitude I and a series of three (3) charge balancing anodic phases (charge balancing phases, also denoted as charge balancing electric pulses herein), which pass ⅓ of the inverted current amplitude I of the therapeutic phase. The therapeutic phase and the charge balancing phases are separated by one (1) inter-phase interval. While electrode 1 passes the therapeutic phase with amplitude I, each of electrode 2, electrode 3 and electrode 4 passes one (1) charge balancing phase with amplitude I/3. While electrode 2 passes the therapeutic phase with amplitude I, each of electrode 1, electrode 3 and electrode 4 passes one (1) charge balancing phase with amplitude I/3. While electrode 3 passes the therapeutic phase with amplitude I, each of electrode 1, electrode 2 and electrode 4 pass one (1) charge balancing phase with amplitude I/3. While electrode 4 passes the therapeutic phase with amplitude I, each of electrode 1, electrode 2 and electrode 3 pass one (1) charge balancing phase with amplitude I/3. After electrode 4 passed one (1) therapeutic phase the cycle starts with electrode 1 again, until terminated. In this way, charge neutrality on any given electrode is maintained, and the sum of current exiting the cathode equals the sum of currents entering anodes at any given time in the waveform.

Figure 9:
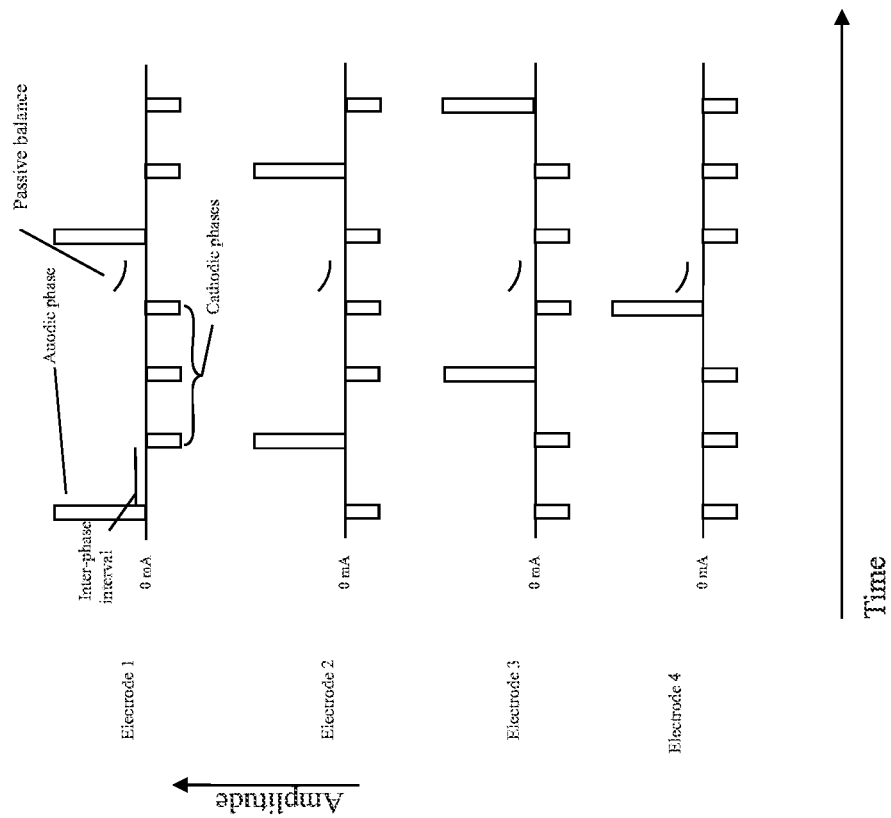
FIG. 9 is a diagram showing another embodiment of the novel stimulation waveform between four (4) electrodes, with anodic preference.

FIG. 9 shows a diagram of another embodiment of the stimulation waveform according to the present invention between four (N=4) therapy electrodes, with anodic preference. The exemplary system/device comprises four (4) electrodes (electrode 1, electrode 2, electrode 3, and electrode 4), each of the three (3) electrodes undergoes a recurring pattern of an anodic phase (therapeutic phase, also denoted as therapeutic electric pulse herein) with a current amplitude I and a series of two (2) charge balancing cathodic phases (charge balancing phases, also denoted as charge balancing electric pulses herein), which pass ⅓ of the inverted current amplitude I of the therapeutic phase. The therapeutic phase and the charge balancing phases are separated by one (1) inter-phase interval. While electrode 1 passes the therapeutic phase with amplitude I, each of electrode 2, electrode 3 and electrode 4 passes one (1) charge balancing phase with amplitude I/3. While electrode 2 passes the therapeutic phase with amplitude I, each of electrode 1, electrode 3 and electrode 4 passes one (1) charge balancing phase with amplitude I/3. While electrode 3 passes the therapeutic phase with amplitude I, each of electrode 1, electrode 2 and electrode 4 pass one (1) charge balancing phase with amplitude I/3. While electrode 4 passes the therapeutic phase with amplitude I, each of electrode 1, electrode 2 and electrode 3 pass one (1) charge balancing phase with amplitude I/3. After electrode 4 passed one (1) therapeutic phase the cycle starts with electrode 1 again, until terminated. In this way, charge neutrality on any given electrode is maintained, and the sum of current entering the anode equals the sum of currents exiting the cathodes at any given time in the waveform.

Alternatively, anodic and cathodic preferences can be mixed or combined in different sequences and alternatively, the amplitudes of the charge balancing phases can have different values for each phase.

Figure 10:
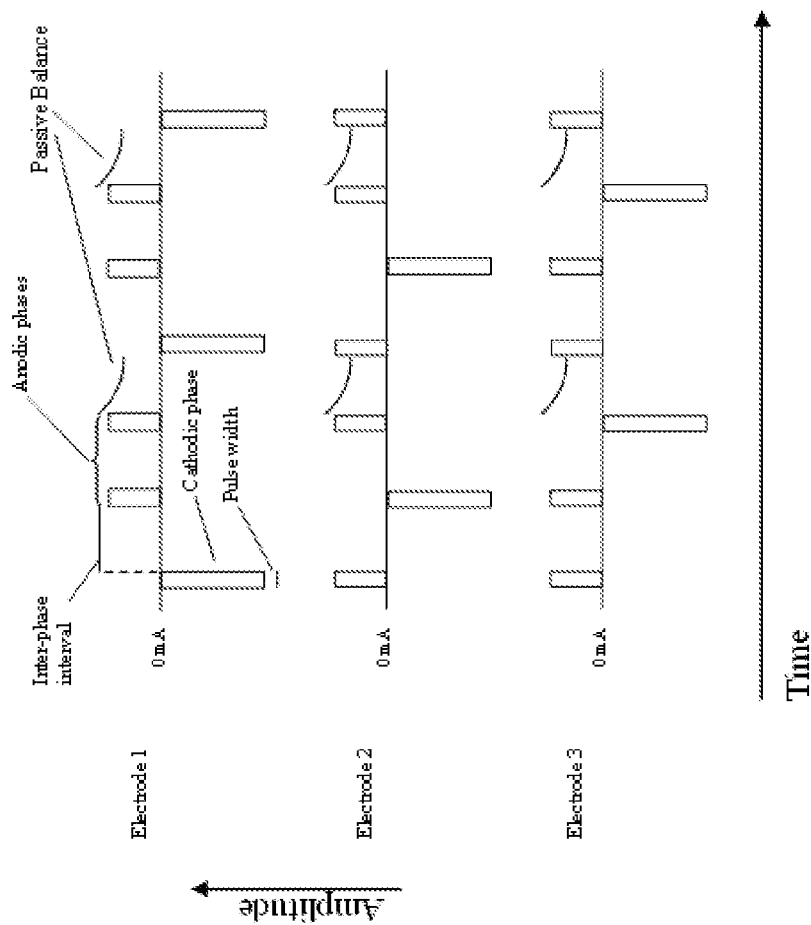
FIG. 10 is a diagram showing another embodiment of the novel stimulation waveform between three (3) electrodes, with cathodic preference.

FIG. 10 shows a diagram of another embodiment of the novel stimulation waveform between three (3) electrodes, with cathodic preference. Stimulation begins with a cathodic phase, contains an inter-phase interval, and ends with a series of anodic (charge balancing) phases, which are aligned with the cathodic phase of a different electrode. In this example, each return electrode (electrode 2 and electrode 3 when electrode 1 stimulates) passes ½ of the amplitude and opposite currents as the currently active cathodic electrode, and the second anodic phase is delivered with passive balancing which may last longer than the cathodic phase of the opposing electrode. In this way, charge neutrality on any given electrode is maintained, and the sum of current exiting the cathode equals the sum of currents entering anodes at any given time in the waveform.

Figure 11:
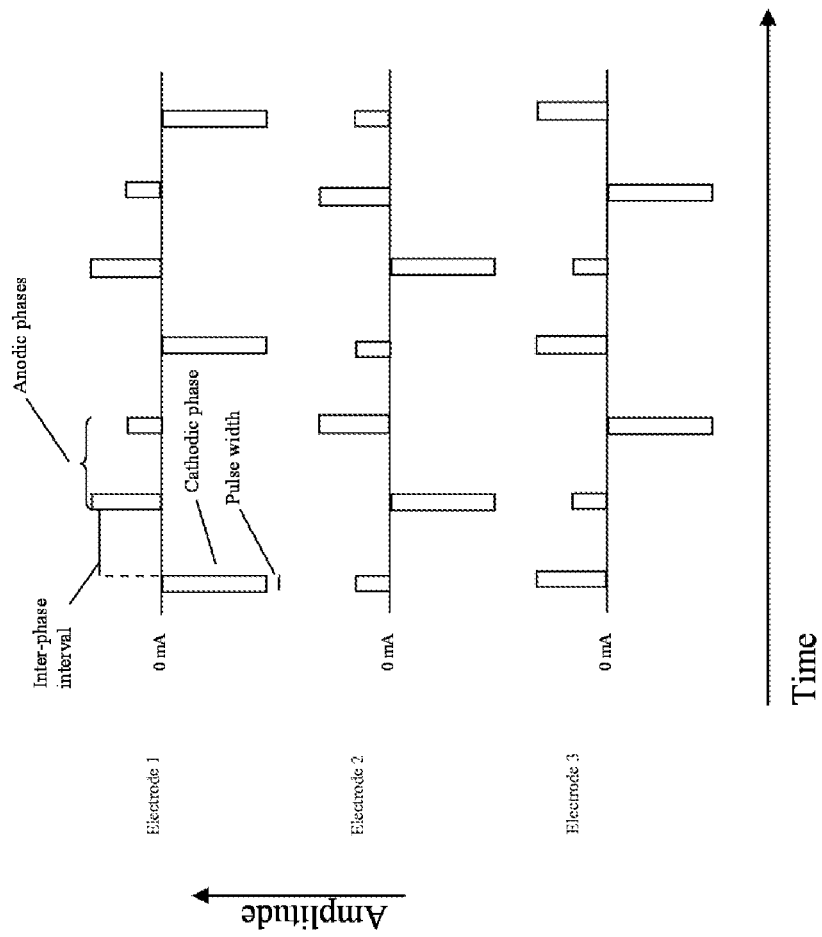
FIG. 11 is a diagram showing another embodiment of the novel stimulation waveform between three (3) electrodes, with cathodic preference.

FIG. 11 shows a diagram of another embodiment of the novel stimulation waveform between three (3) electrodes, with cathodic preference. Stimulation begins with a cathodic phase, contains an inter-phase interval, and ends with a series of anodic (charge balancing) phases, which are aligned with the cathodic phase of a different electrode. In this example, return currents do not share equal current yet the sum of their current equals the amplitude and is opposite the current of the currently active cathodic electrode. In this way, charge neutrality on any given electrode is maintained, and the sum of current exiting the cathode equals the sum of currents entering anodes at any given time in the waveform.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

The invention claimed is:

1. An implantable medical device for delivering neurostimulation, comprising:
   a pulse generator including an application specific integrated circuit (ASIC);
   a number N of electrodes, wherein N is equal to or larger than 3; and
   said ASIC configured to deliver, via each electrode of the N electrodes of the implantable medical device, a set of pulses including a therapeutic electric pulse and a number of N−1 charge balancing electric pulses, wherein the charge balancing electric pulses of the electrode each have a polarity being opposite to a polarity of the therapeutic electric pulse of the electrode, wherein a current of the therapeutic electric pulse is equal to a sum of currents of the charge balancing electric pulses.

2. The implantable medical device according to claim 1, wherein the implantable medical device is configured to deliver the therapeutic electric pulse to a first of the N electrodes and to deliver a charge balancing electric pulse in all the other N−1 electrodes at a time of delivery of the therapeutic electric pulse in the first of the N electrodes.

3. The implantable medical device according to claim 1, wherein said pulse generator is configured to deliver the therapeutic electric pulse with a current amplitude of I, and wherein the charge balancing electric pulses are delivered with a current amplitude of I/(N−1).

4. The implantable medical device according to claim 1, wherein said pulse generator is configured to deliver the charge balancing electric pulses with varied current amplitudes.

5. The implantable medical device according to claim 1, wherein said pulse generator is configured to deliver the therapeutic electric pulse and the charge balancing electric pulses such that an integrated average charge delivered by the therapeutic electric pulse and the charge balancing electric pulses is zero over time.

6. The implantable medical device according to claim 1, wherein said pulse generator is configured to deliver the therapeutic electric pulse such that a time interval between any two successive said therapeutic electric pulses from different electrodes is 1/Nf, where N is the number of said electrodes and f is the frequency of the set of pulses.

7. The implantable medical device according to claim 1, wherein said pulse generator is configured to deliver the therapeutic electric pulse and the charge balancing electric pulses such that the therapeutic electric pulse and the charge balancing electric pulses are separated by inter-pulse intervals.

8. The implantable device according to claim 7, wherein said pulse generator is configured to deliver a passive-balance charge via the N electrodes during at least one of the inter-pulse intervals.

9. The implantable medical device according to claim 1, wherein the implantable medical device is configured to deliver the neurostimulation in a form of spinal cord stimulation.

10. The implantable medical device according to claim 1, wherein an amplitude I of the therapeutic electric pulse lies within a range from 0.1 mA to 20.0 mA.

11. The implantable medical device according to claim 1, wherein the implantable medical device provides at least one parameter configuration for the neurostimulation, wherein the parameter configuration is stored in the device.

12. The implantable medical device according to claim 1, wherein the implantable medical device provides at least one parameter configuration for spinal cord stimulation, wherein the parameter configuration is stored in the implantable medical device.

13. The implantable medical device according to claim 1, wherein said ASIC is configured to perform a biphasic stimulation of a respective electrode of the plurality of N electrodes by at least one of:
   configuring a programmable voltage $V_{IStim}$ to provide a sourcing current through the respective electrode; and/or
   configuring a programmable voltage $V_{NCounter}$ to control a sinking current through the respective electrode; and/or
   configuring a first switchable element to selectively connect the respective electrode to the programmable voltage $V_{IStim}$; and/or configuring a second switchable element to selectively connect the respective electrode to the programmable voltage $V_{NCounter}$; and/or configuring a third switchable element to selectively connect a mid-voltage reference $V_{Mid}$ to the respective electrode for passive charge balancing; and/or controlling said sourcing current and said sinking current being independently at each electrode of the plurality of N electrodes to permit delivering simultaneous multi-electrode therapy with active charge balancing.

14. A method for delivering neurostimulation using a number N of electrodes of an implantable medical device, wherein N is equal to or larger than 3, which comprises the step of:

using an application specific integrated circuit (ASIC) of the implantable medical device to deliver via each electrode, a set of pulses including a therapeutic electric pulse and a number of N−1 charge balancing electric pulses, the charge balancing electric pulses of the electrode each have a polarity that is opposite a polarity of a preceding therapeutic electric pulse of the electrode, and wherein for each said electrode a current of each therapeutic electric pulse is returned in the other N−1 electrodes.

15. The method according to claim 14, wherein for the therapeutic electric pulse of each of the N electrodes, a charge balancing electric pulse in all the other N−1 electrodes is delivered at a time of a delivery of the therapeutic electric pulse.

16. The method according to claim 14, wherein the charge balancing electric pulses have an amplitude of I/(N−1).

17. The method according to claim 14, wherein the charge balancing electric pulses have variable amplitudes.

18. The method according to claim 14, wherein an additional passive balance pulse is delivered in at least one inter-pulse interval.

19. The method according to claim 14, which further comprises delivering the therapeutic electric pulses and the charge balancing electric pulses such that an integrated average charge delivered by the therapeutic electric pulses and the charge balancing electric pulses is zero over time.

20. The method according to claim 14, wherein the ASIC delivers the set of pulses by at least one of:

configuring a programmable voltage $V_{IStim}$ to provide a sourcing current through the respective electrode; and/or configuring a programmable voltage $V_{NCounter}$ to control a sinking current through the respective electrode; and/or configuring a first switchable element to selectively connect the respective electrode to the programmable voltage $V_{IStim}$; and/or configuring a second switchable element to selectively connect the respective electrode to the programmable voltage $V_{NCounter}$; and/or configuring a third switchable element to selectively connect a mid-voltage reference $V_{Mid}$ to the respective electrode for passive charge balancing; and/or controlling said sourcing current and said sinking current being independently at each electrode of the plurality of N electrodes to permit delivering simultaneous multi-electrode therapy with active charge balancing.

\* \* \* \* \*